United States Patent [19]

Vidal

[11] Patent Number: 5,269,773
[45] Date of Patent: Dec. 14, 1993

[54] TIGHT COUPLING DEVICE FOR OSTOMY

[75] Inventor: Jose M. P. Vidal, Cornella de Llobregat, Spain

[73] Assignee: Industrias Palex, S.A., Barcelona, Spain

[21] Appl. No.: 829,054

[22] PCT Filed: Jun. 7, 1990

[86] PCT No.: PCT/ES90/00018
§ 371 Date: Feb. 5, 1992
§ 102(e) Date: Feb. 5, 1992

[87] PCT Pub. No.: WO91/18566
PCT Pub. Date: Dec. 12, 1991

[51] Int. Cl.$^5$ .............................................. A61F 5/44
[52] U.S. Cl. .................................. 604/342; 604/338; 604/339
[58] Field of Search .................. 604/332–345, 604/905

[56] References Cited

U.S. PATENT DOCUMENTS 5,004,464  4/1991  Leise ................................. 604/338

FOREIGN PATENT DOCUMENTS 2148716  6/1985  United Kingdom ................ 604/339

Primary Examiner—Randall L. Green
Assistant Examiner—Rob Clarke
Attorney, Agent, or Firm—Abelman Frayne & Schwab

[57] ABSTRACT

The device object of the present invention relates to a sealed coupling for ostomy, of the type applicable in closing systems and which includes a collecting bag provided with a central orifice which may be brought face to face to a stoma and surrounded by an annular coupling element joined to the wall of said bag, which coupling element has a double wall defining a channel with its opening oriented towards the stoma, and which cooperates with a second annular coupling element integral with a plate adhered to the skin of the user around the stoma, allowing a coupling/uncoupling as desired by the user. To this effect, there is provided an annular tubular neck adhered to the user's skin coupled in a conduit defined by an also annular double wall joined around the stoma-facing orifice of the collecting bag.

4 Claims, 3 Drawing Sheets

TIGHT COUPLING DEVICE FOR OSTOMY

The present invention relates to a tight coupling device for ostomy.

AREA OF THE INVENTION

As is known, in some gastrointestinal or urinary surgical operations the patients have artificial openings made to which bags for receiving the residues are connected. These artificial openings are known as colostomies, urostomies or ileostomies, commonly designated by the term ostomy.

The device of this invention relates to a tight coupling for ostomy, of the type applicable in assemblies for ostomy which comprise a collecting bag with a central orifice, juxtaposable to a stoma and surrounded by an annular coupling element connected to the wall of said bag, which element has a double wall defining a channel with its opening oriented toward the stoma, which cooperates with a second annular coupling element integral with a plate adhering to the user's skin around the stoma, permitting very simple and convenient coupling/uncoupling at the user's discretion.

HISTORY OF THE INVENTION

The collecting ostomy bags and the accessories attached to them are preferably made of plastic materials, in view of their flexible and impermeable characteristics, among others.

The closure systems formed by obturation elements in the form of male and female ribs, both of plastic, capable of nesting one in the other offering an efficient closure and facilitating the opening of flexible bags generally of plastic material, are known and widely used in a variety of industrial sectors.

These types of closure systems are fully described by KABUSHIKI KAISHA SEISAN NIPPON-SHA, contained in Spanish Patents No. 279,517 of 1962 and Certificate of Addition No. 332,468 of 1966, and by MINIGRIF EUROPE AKTIESEISKAB contained in Spanish Patent No. 330,627 of 1967.

More concrete antecedents of the present invention in the sector where the latter applies are in the first place German patent No. 2,812,833 and in particular the embodiment thereof which is covered in Spanish Utility Model No. 238,930. Said patent concerns a device of the cited type which comprises two semirigid annular coupling elements, one joined to the plate which in turn adheres to the user's skin in the zone surrounding the stoma, and the second annular element fastened to a collecting bag, adopting a transverse section which defines a channel with its orifice oriented toward the stoma and with a projection on its outer wall which cooperates in interlock with a shoulder of a tubular neck which is integral with the first-mentioned annular element, so that as the two annular elements are being coupled, the neck of the first enters into the second having an obturation lip and providing a hermetic closure.

The device referred to has a first disadvantage relating to the cleaning of the annular element connected to the plate adhering to the user, since the shutting lip defines a cavity where residues may be retained, difficult to reach, and in any event involving manipulations which add to the user's discomfort.

Also, the proposed coupling will make it necessary for the user or the therapist to exert traction or apply pressure whenever the collecting bag must be replaced, causing the patient discomfort or pain, which should be eliminated.

Thirdly, the tubular neck of the described device is not rigid enough for the coupling to be classified as secure so that the bag will not come loose unintentionally in general by the patient's movements.

As to the imperviousness of the device it may also be objected that the same is supported exclusively by a lip defined on the element integral with the plate or patch adhering to the user and which is not changed every time the collecting bag is replaced, for which reason said lip may in time lose its effectiveness, with the possible deposition of residues in the concavity that it defines, as emphasized above.

A second antecedent of the invention can be found in U.S. Pat. No. 4,419,100, in which is discussed at length the problem of the necessary rigidity of the tubular neck combined with the flexible properties of the annular coupling elements necessary for simplifying and facilitating the tasks of replacement of the bag.

Although the solution offered in that patent gives results superior to those of the previously considered patent, here the risk exists of possible depositions of residues inside the canal which receives the tubular neck, thereby complicating the task of replacing the bag.

Also the cost of this second device is considerable in view of the manner of connecting the second coupling element to the plate adhering to the patient.

Lastly, the walls of the canal of the annular element that has the neck of the other annular element inserted in it have an equal or equivalent width, so that the free passage of the opening toward the bag is reduced, and the end of the inner wall forms a stepped connection which may favor the deposit of residues.

DESCRIPTION OF THE INVENTION

The coupling device according to the present invention eliminates the disadvantages pointed out, giving a remarkable imperviousness between the two closure elements of male and female configuration that form it.

For this there has been provided an annular element in the form of a tubular neck of predetermined cross section, integral with the plate adhering to the user's skin, which tubular neck will be coupled on a canal defined by a double wall, also annular, integrally linked around the orifice juxtaposable to the stoma of the collecting bag.

Said tubular neck possesses an inverted truncated cone-shaped inner surface, its wall presenting a maximum width at the interlocking zone and its outer face defines a protuberant profile having at its base circumferentially equidistant slots, from which originate outwardly a laminar lug of flexible condition, and inwardly a second laminar lug.

The annular element which forms said canal connected to the wall of the collecting bag, around the orifice thereof facing the stoma, has a rectangular trapezoidal cross-section, with a constriction in its mouth caused by an inward protuberance of the canal, at the edge of the outer wall, which is substantially rigid, with an annular recess in its outer face, while the second wall limiting the canal is thin and flexible so that it can easily adapt to the inverted truncated cone-shaped inner face of the tubular neck of the second coupling element, without formation of a step on the corresponding end edge.

The coupling between the two annular elements occurs by means of the fitting of the tubular neck against the bottom of the annular channel, offering imperviousness in at least three differentiated annular zones of the inner surface of the annular channel—a first one at the end of the inner wall of the annular channel by slight deformation against the lower end of the first inclined section of the tubular neck; a second one by juxtaposition of the distal end of the tubular neck, parallel to the base thereof, against the bottom of the annular channel; and a third one by coincidence of the protuberance of the outer wall of the tubular neck defined by the triangular profile against the protuberance of the end of the outer wall of the annular canal.

The solution according to the present invention offers optimum results, mainly by its tightness, easy handling and cleaning, as compared with the solutions known until now.

In fact, the coupling between the two annular elements occurs with slight pressure, thereby obtaining absolute tightness to the exterior, through the means which bring about said union, and ensuring rapid passage of the stools between the interior of the user's stoma and the interior of the bag.

The inclination of the first section of the interior of the tubular annular neck in juxtaposition with the end of the inner wall of one of the two walls which form the annular channel makes it easy for the stools to get quickly into the interior of the bag. Also, the described structure does not permit the settling of the stools in this intermediate section.

The materials which constitute the rings referred to, as well as the bag itself, ensure an elastic deformation necessary for the user's comfort, without thereby altering the stated characteristics.

Besides the foregoing elements, the device comprises others which will be pointed out below.

BRIEF DESCRIPTION OF THE DRAWINGS

The annexed drawings, given only by way of example, will help to better understand the invention, the characteristics which it presents, and the advantages that it is able to offer.

DETAILED DESCRIPTION OF A PREFERRED EMBODIMENT OF THE INVENTION

Figure 1:
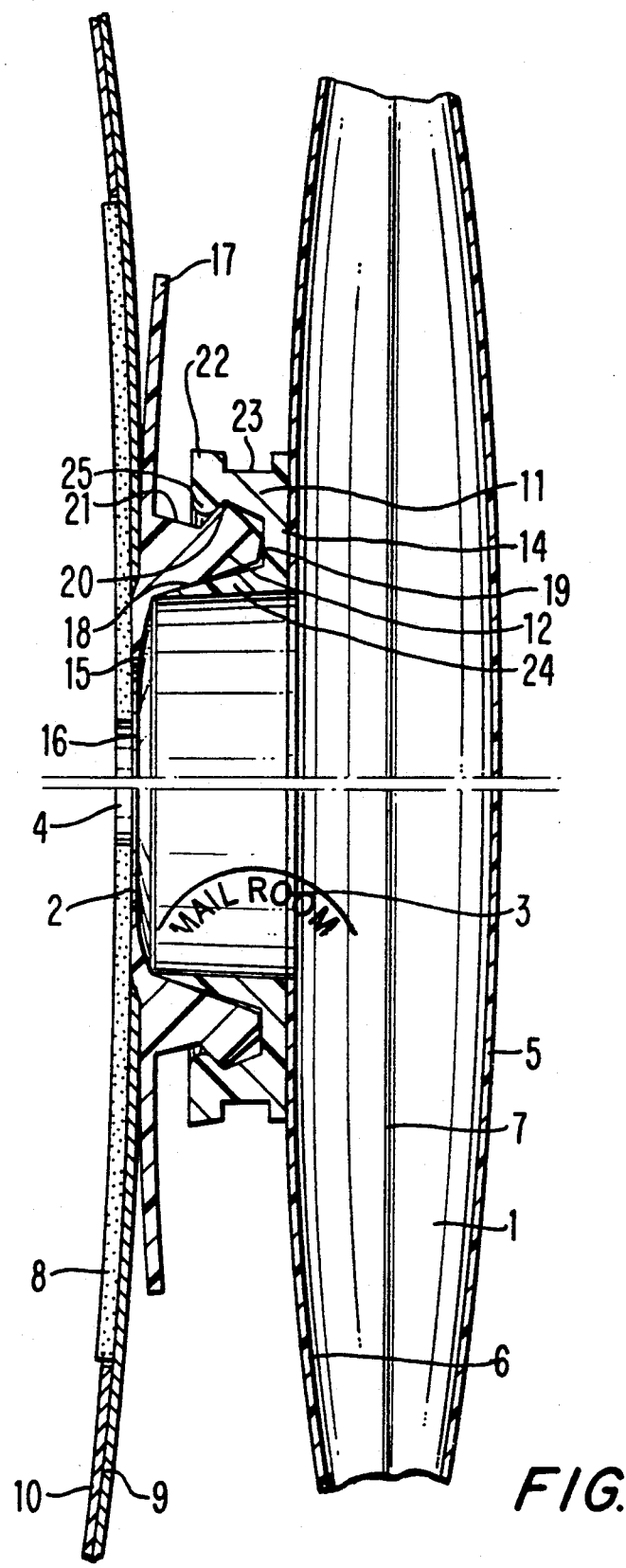
FIG. 1 is a view in transverse section of a device according to the present invention, with the two annular elements coupled.
Figure 2:
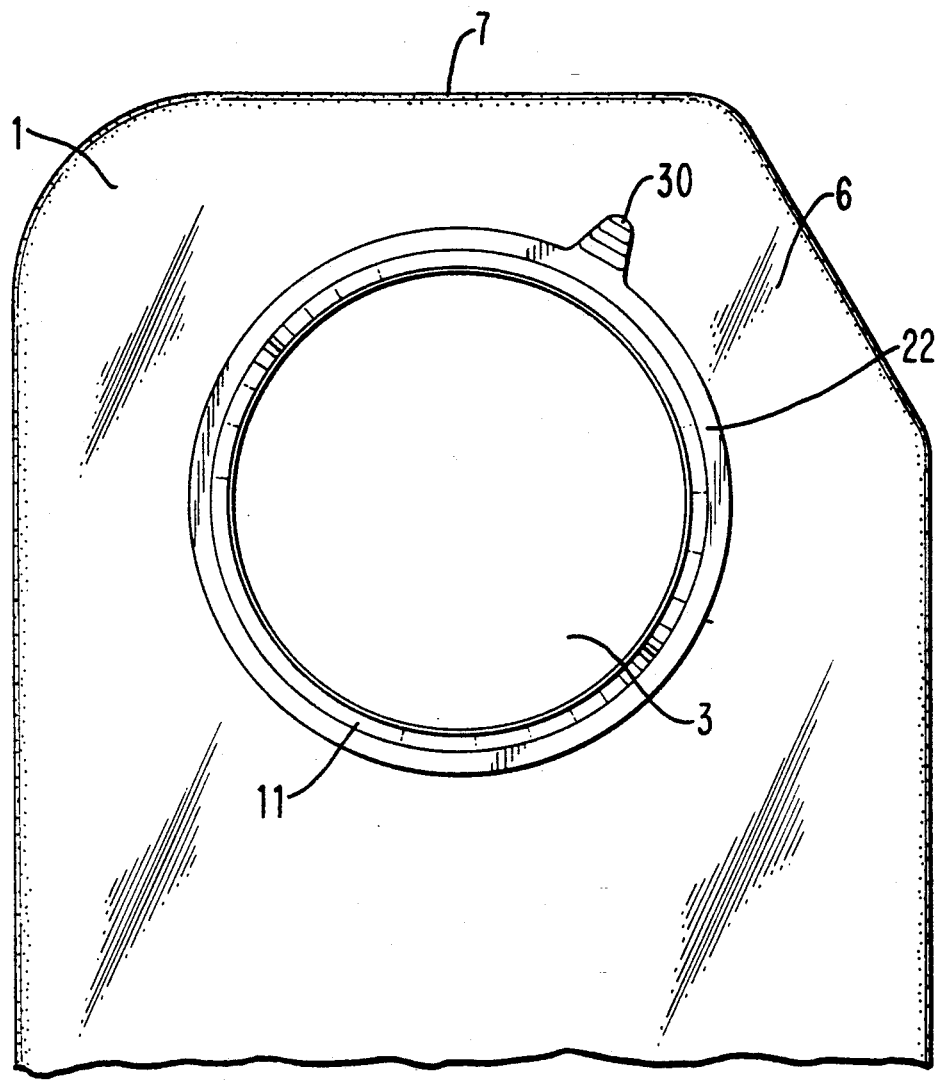
FIG. 2 is a plan view of the collecting bag provided with the annular channel.

In FIG. 1 is shown a coupling device according to the present invention, formed by the collecting bag 1 and the plate 2, both provided with the orifices 3 and 4 juxtaposable to the patient's stoma.

The collecting bag 1 is formed by two identical flexible sheets, perimetrically heat-sealable at 7, the inner sheet 6 comprising the orifice 3 which connects it with its interior.

Plate 2 is formed by a first conventional ring 8, of a material known commercially in the sector as "karaya" of therapeutic characteristics, extraneous to the present invention. This ring is covered by a second ring 9 of larger diameter of a cellulose material which on its inner face comprises an adhesive, protected by the ring 10 of paper or the like, for its adhesion on the surface of the skin that surrounds the stoma thereof.

The materials that constitute the bag 1 are of plastic nature and laminar condition, such as polyethylene, PVC, polyamide or the like, or a compound of the type formed by polyethylene/EVA/polyvinyl chloride or similar.

The collecting bag 1 is coupled to plate 2 through the annular channel 11 and the tubular neck 12.

The annular channel 11 and the tubular neck 12 may be made of high or low density polyethylene or of ethylene and vinyl acetate copolymer (EVA) or polyvinyl chloride (PVC), and obtained by molding.

The orifice 3 provided in the collecting bag 1 is of a diameter equal to or greater than the orifice defined by the annular channel 11, as long as the contour of the orifice of sheet 6 can be joined with the basal surface 14 of the annular channel 11 integrally in conventional manner by heat.

The tubular neck 12 presents in its basal zone and oriented inwardly a lug 15 which in turn defines a central orifice 16 facing the orifice 4 provided in the annular plate 8. The union between the tubular neck 12 and plate 2 is obtained by heat between the end of the inner lug 15 of the tubular neck 12 and the inner perimeter of ring 9, being joined to the annular plate 8 by the previously mentioned means.

From the base of the tubular neck 12 originates outwardly a laminar lug 17, the usefulness of which will be explained later.

The tubular neck 12 itself has a continuous general section formed by an inner lug 15 followed by a f first inclined section 18, a second section 19 parallel to the base of the tubular neck 12, followed by a triangular profile 20, and ending in a section 21 substantially perpendicular to the base which extends outwardly through the laminar lug 17.

The annular channel 11 connected by the surface 14 to the sheet 6 of the collecting bag 1 is turned toward the stoma of the patient, presenting in section, its substantially rigid outer wall 22 and with an annular recess in its outer face of rectangular section 23, and its much thinner inner wall 24, of triangular profile inverted from the surface 14, slightly protrucing relativve to the outer wall 22.

Internally, the annular channel 11 comprises on the outer wall 22 a protuberance 25 at its lower end, the usefulness of which will be described later.

Figure 4:
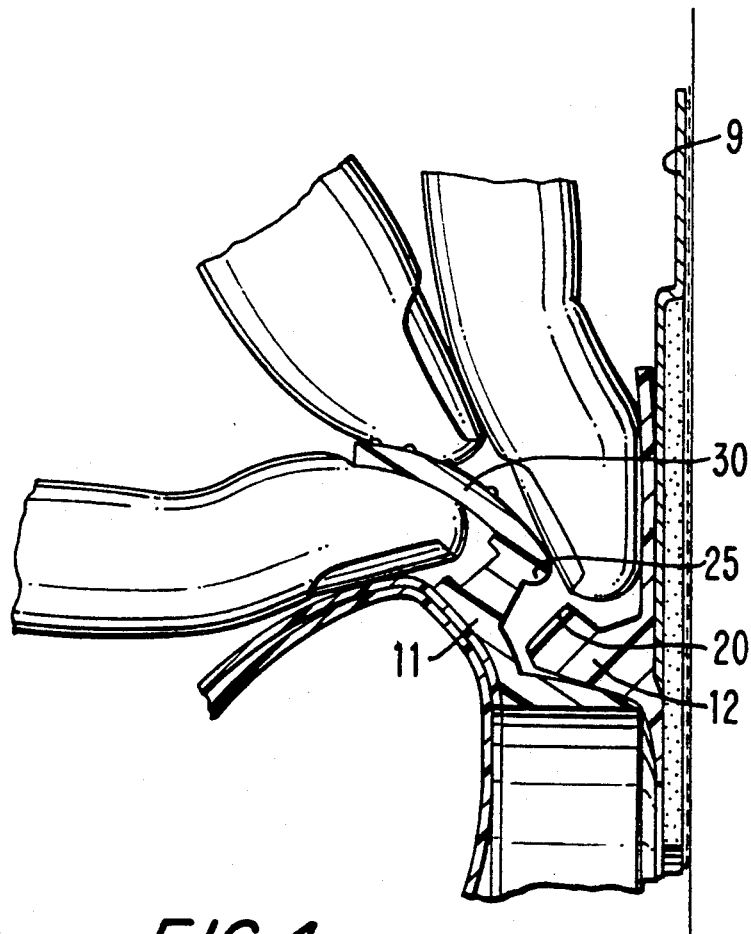
FIG. 4 is a sectional view of the annular channel with the tubular neck uncoupled.

Externally, the annular channel 11 is provided with a lug 30, as shown in FIG. 4, the usefulness of which will be described later.

Figure 3:
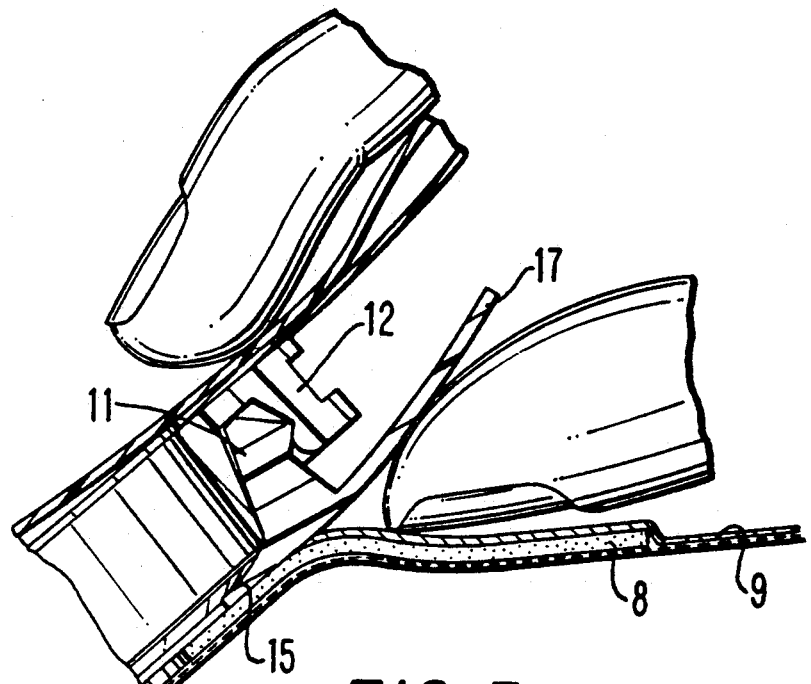
FIG. 3 is a sectional view of the annular channel cooperating with the tubular neck during the phase of installation of the bag connected to tubular neck.

The coupling between the annular channel 11 and the tubular neck 12 is obtained by means of the insertion of the former against the latter, as shown in FIG. 3.

The annular plate 8 will place itself around the patient's stoma and will stay connected therewith by means of the ring 9 adhering on the patient's skin, allowing the tubular neck 12 to be positioned reliably.

As the tubular neck 12 is connected to the ring 9 by the end of the inner lug 15, and as the materials that constitute the parts are flexible, the user's thumb can be positioned between the outer laminar lug 17 of the tubular neck 12 and the adhesive ring 9, as shown in FIG. 3.

By its free end, the tubular neck 12 is able to receive the bottom of the annular channel 11 and by slight pressure between both parts through the positioning referred to, with the index finger of the same hand on the outer face of the bag against the surface 14 of the annular channel 11, almost without exerting force on plate 8 and the peristomal zone.

The coupling between the two annular elements receives an imperviousness in three differentiated annular zones:

A first one between the end of the triangular inner wall 24 inverted from the surface 14 of the annular channel 11, by slight deformation on the first inclined section 18 of the tubular neck.

A second zone by juxtaposition of the section 19 parallel to the base of the tubular neck 12 against the inner bottom of the annular channel 11, and A third and last zone through the protruberance 25 of the inner lower end of the outer wall of the annular channel 11, with the outer triangular projection 20 of the tubular neck 12.

FIG. 4 shows how to proceed for the uncoupling between the annular channel 11 and the tubular neck 12. Thus, by slight pressure outward with the fingers of one hand through lug 30 of annular channel 11, and pressing the fingers of the other hand on the surface of the outer laminar lug 17 of the tubular neck 12, it is feasible to release, by deformation, the protuberance 25 of the inner lower end of the outer wall of the annular channel 11 from the outer triangular projection 20 of the tubular neck 12.

With the coupling of the two annular elements, the inclination of the inner triangular wall 24 inverted from the surface 14 of the annular channel 11 by slight deformation on the first inner inclined section 18 of inverted truncated cone shape of the tubular neck 12 cooperates definitively to ensure the tightness of the assembly, as it not only does not permit the deposit of the stools on the same distance existing between the end of that inclined section and the small angle defined by the first inclined inner section 18 and the inner lug 15 of the tubular neck 12, but it effectively helps owing to its inclination to facilitate the path of the stools from the stoma toward the interior of the collecting bag 1.

I claim:

1. A coupling for an ostomy device, of the type including a first annular element connected to an adhesive backing plate to be adhered to a user's skin in surrounding relation with a stoma, and, a second annular element for interengagement with said first annular element and which is connected to a collecting bag, further including, said first annular element including an inner wall of truncated conical shape diverging from said backing plate to an open end of said first annular element, an end wall of said first annular element extending radially outwardly of said first annular element at said open end of said first annular element, and an outer wall of truncated conical shape of said first annular element diverging from said radially outwardly extending end wall of said first annular element, thereby to define a free end of said first annular element of substantially trapezoidal cross section, said second annular element including a thin and flexible axially extending annular wall having a conical outer surface for sealing engagement with said inner truncated conical wall of said first annular element, a radially extending wall for sealing engagement with said radially outwardly extending wall of said first annular element, and an axially extending conical wall diverging from an outer periphery of said radially extending wall of said second annular element for sealing engagement with said outer wall of said first annular element, whereby to provide three separate zones of sealing between said first and second annular elements;

said second annular element being formed from a pliable material of greater flexibility than said first annular element, said conical axially extending wall of said second annular element being axially longer than said truncated conical inner wall of said first element and providing an interference fit within said truncated conical inner wall of said first annular element.

2. The coupling device of claim 1, in which said axially extending annular wall of said second annular element is of an axial length sufficient for said conical outer surface to cover the entire surface of said truncated conical inner wall of said first annular element.

3. The coupling of claim 1, further including an annular member extending from a base of said first annular element and which provides an attachment of said first annular element to said adhesive backing plate, said annular member being of greater flexibility than said first annular element.

4. The coupling device of claim 1, wherein said first annular element defines a peripherally extending channel for the reception of a radially inwardly extending flange on the free end of said axially extending conically divergent wall of said second annular element.

* * * * *

UNITED STATES PATENT AND TRADEMARK OFFICE
CERTIFICATE OF CORRECTION

PATENT NO. : 5,269,773
DATED : December 14, 1993
INVENTOR(S) : Jose M.P. Vidal

It is certified that error appears in the above-indentified patent and that said Letters Patent is hereby corrected as shown below:

On the title page: Item [75] change "Jose M.P. Vidal" to --Jose M. Pascual Vidal, Cornella de Llobregat, Spain Signed and Sealed this Sixteenth Day of August, 1994

BRUCE LEHMAN

*Attest:*

*Attesting Officer*     *Commissioner of Patents and Trademarks*